United States Patent [19]

Keller-Juslen et al.

[11] Patent Number: 4,478,831

[45] Date of Patent: Oct. 23, 1984

[54] ANTIBIOTICS, PHARMACEUTICAL COMPOSITIONS AND METHOD OF USE

[75] Inventors: Camilla Keller-Juslen; Max Kuhn; Hamilton D. King, all of Basel, Switzerland

[73] Assignee: Sandoz Ltd., Basel, Switzerland

[21] Appl. No.: 376,904

[22] Filed: May 10, 1982

Related U.S. Application Data

[63] Continuation-in-part of Ser. No. 196,577, Oct. 14, 1980, abandoned, which is a continuation-in-part of Ser. No. 46,287, Jun. 7, 1979, abandoned.

[30] Foreign Application Priority Data

Jun. 8, 1978 [CH] Switzerland ..................... 6282/78

[51] Int. Cl.³ ................ A61K 31/71; C07H 17/00; C12P 19/62

[52] U.S. Cl. .................................. 424/181; 536/16.8; 536/18.1; 424/117; 435/105; 435/76

[58] Field of Search .............. 424/181, 117; 536/16.8, 536/18.1

[56] References Cited

U.S. PATENT DOCUMENTS

| | | | |
|---|---|---|---|
| 4,078,056 | 3/1978 | Weinstein et al. | 424/115 |
| 4,137,224 | 1/1979 | Taplin et al. | 536/16.8 |
| 4,326,054 | 4/1982 | Umezawa et al. | 536/16.8 |

Primary Examiner—Johnnie R. Brown
Attorney, Agent, or Firm—Gerald D. Sharkin; Robert S. Honor; Thomas O. McGovern

[57] ABSTRACT

The antibiotics S 54832/A-I, S 54832/A-II, S 54832/A-III and S 54832/A-IV are obtained from a new *Micromonospora globosa* strain.

6 Claims, 11 Drawing Figures

ANTIBIOTICS, PHARMACEUTICAL COMPOSITIONS AND METHOD OF USE

This is a continuation in part of application Ser. No. 196,577, Oct. 14, 1980, now abandoned, which in turn is a continuation in part of our application Ser. No. 46,287 filed June 7, 1979 now abandoned.

The present invention relates to the related compounds S 54832/A-I, S 54832/A-II, S 54832/A-III and S 54832/A-IV.

In accordance with the invention S 54832/A-I, S 54832/A-II, S 54832/A-III and/or S 54832/A-IV is obtained by cultivating an S 54832/A-I and/or S 54832/A-II and/or S 54832/A-III and/or S 54832/A-IV producing strain, e.g. of Micromonosporaceae e.g. Micromonospora e.g. *Micromonospora globosa*, in the presence of a culture medium.

Figure 1:
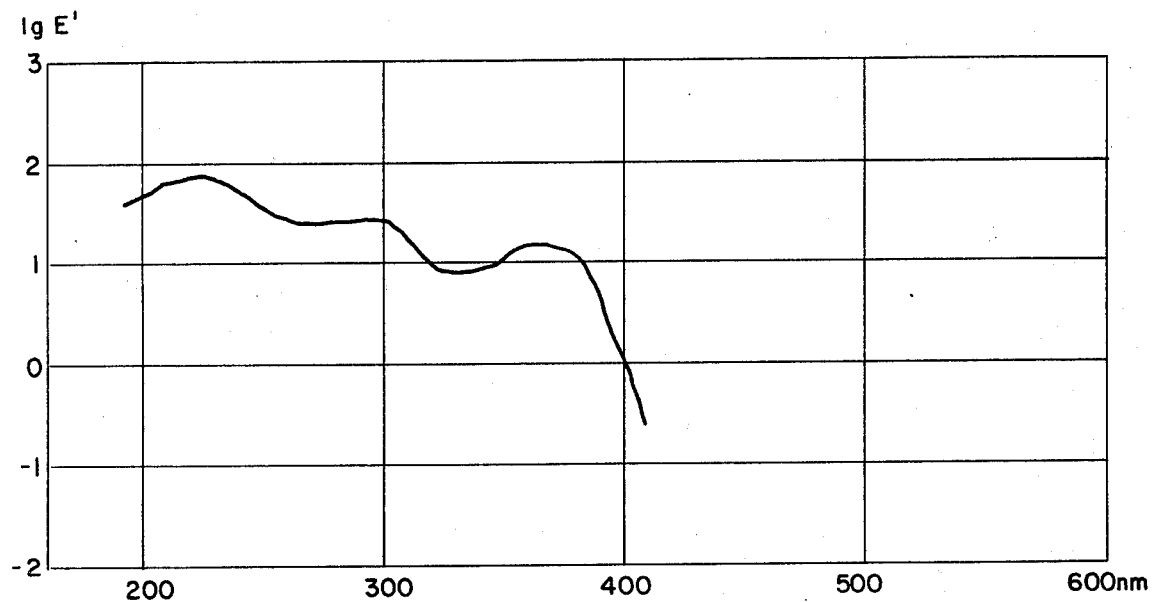
Figure 2:
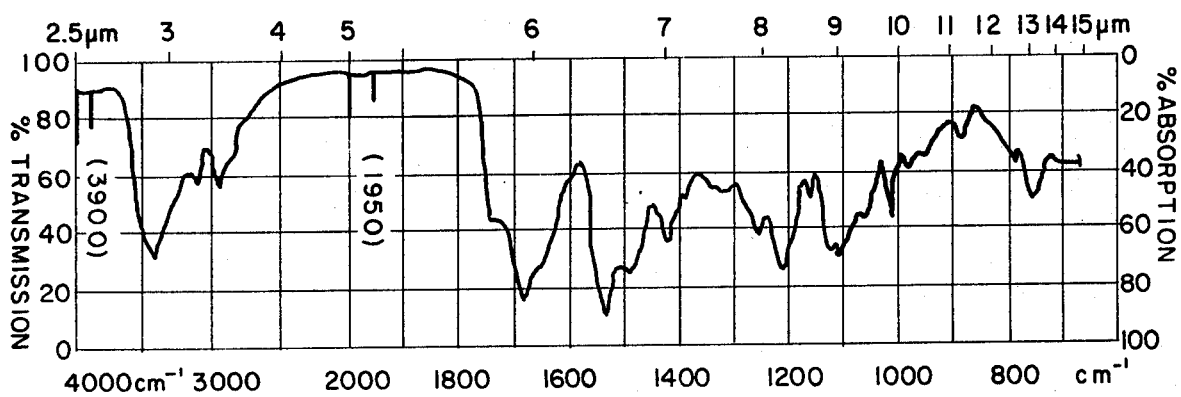
Figure 3:
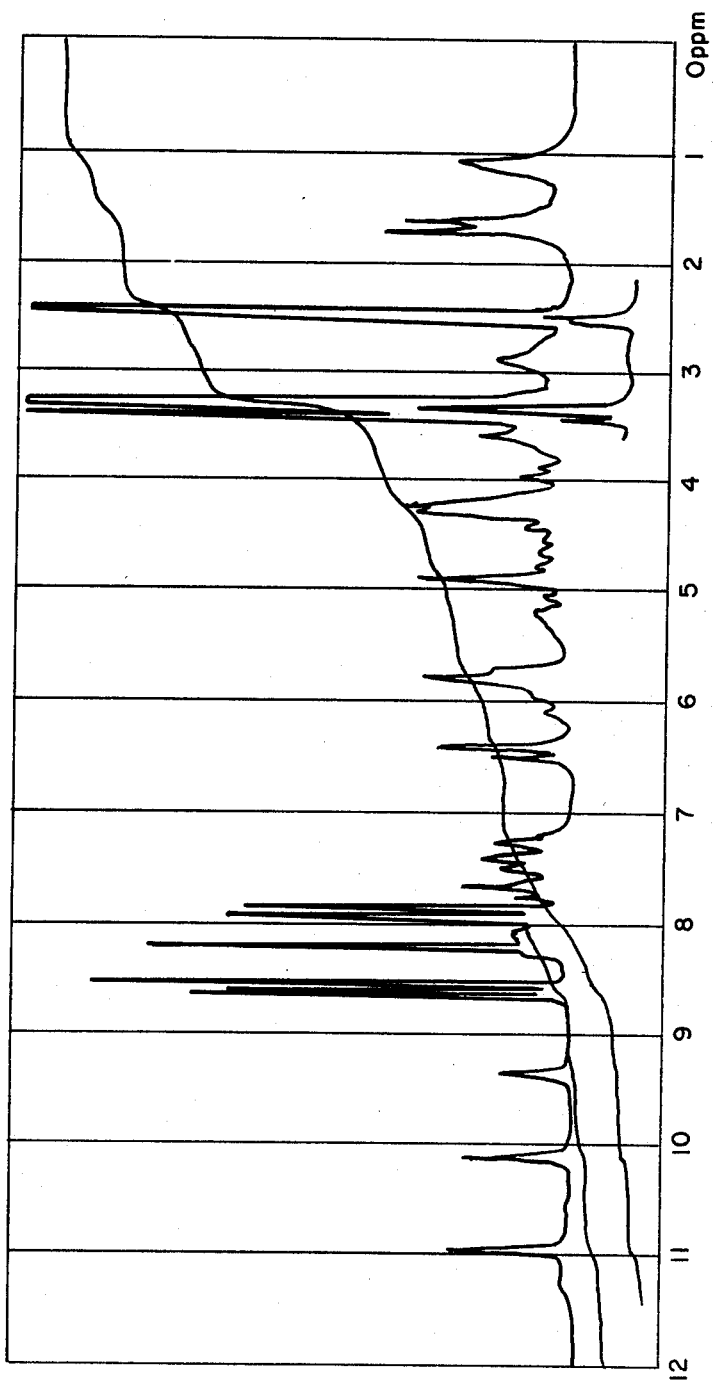

The compounds S 54832/A-I, S 54832/A-II, S 54832/A-III and S 54832/A-IV exhibit the following approximate characteristics (It will be appreciated that all data are approximate and subject to the usual margins of experimental error and variations due to differing degrees of purity.):

S 54832/A-I
Light yellow amorphous powder
M.P.>310°
$[\alpha]_D^{20} = +118.7°$ (c=1.140 in pyridine) formula $C_{59}, H_{55}, N_{13}, O_{19}, S_5$ (1410.50)
Analysis: Found C 50.2, H 4.2, N 13.1, O 21.7, S 11.3% Calculated C 50.2, H 3.9, N 12.9, O 21.6, S 11.4
UV spectrum in acetonitrile, see FIG. 1.
λmax 219 nm log $\epsilon'=1.86$, 287 nm log $\epsilon'=1.41$, 364 nm log $\epsilon'=1.13$.
IR spectrum (in KBr), see FIG. 2.
$^1$H-NMR spectrum in DMSO, 90 MHz with tetramethylsilane as internal standard, see FIG. 3.
$^{13}$C-NMR spectrum in DMSO on a BRUKER HX-90E spectrometer at 22.63 MHz (internal standard TMS=0 ppm), see the following Table I.

TABLE 1

| $^{13}$C—NMR spectrum of S 54832/A-I 100 mg in 1.2 ml DMSO + TMS | |
|---|---|
| 171.18 | 112.23 |
| 168.25 | 111.06 |
| 167.73 | 103.78 |
| 167.21 | 95.53 |
| 167.02 | 79.67 |
| 165.07 | 74.93 |
| 163.77 | 73.56 |
| 160.91 | 69.40 |
| 160.07 | 67.39 |
| 159.94 | 65.25 |
| 159.42 | 63.10 |
| 158.31 | 62.52 |
| 153.89 | 57.45 |
| 150.97 | 55.95 |
| 149.67 | 49.52 |
| 149.41 | 25.80 |
| 148.56 | 17.80 |
| 147.39 | 13.58 |
| 142.65 | |
| 134.91 | |
| 134.39 | |
| 129.78 | |
| 129.20 | |
| 128.16 | |
| 127.25 | |
| 126.47 | |
| 125.36 | |
| 124.19 | |
| 123.09 | |
| 119.97 | |

TABLE 1-continued

| $^{13}$C—NMR spectrum of S 54832/A-I 100 mg in 1.2 ml DMSO + TMS | |
|---|---|
| 119.38 | |

Solubility:

Slightly soluble in dimethylformamide, acetonitrile, dioxane, pyridine, dimethylsulphoxide; fairly soluble in chloroform; sparingly soluble in methanol, ethanol and insoluble in water and hexane.

Amino acid analysis

Aside from non-identified amino acids, the amino acid analysis revealed an amino acid having the same retention time as threonine.

pK and Equivalent weight determination $pK_1=7.65$; (approximate equivalent weight: 1521) $pK_2 \geqq 10.69$ obtained when 6.403 mg of S 54832/A-I dissolved in 2 ml methylcellosolve/water (84:16) were titrated with 0.1N tetramethylammonium hydroxide in water.

S 54832/A-II

Figure 4:
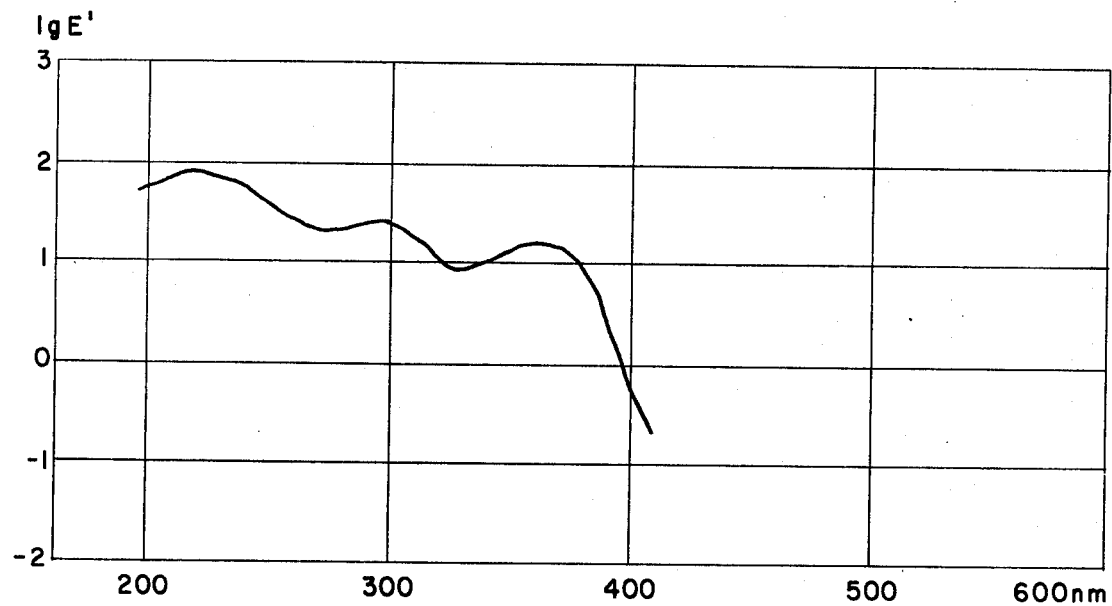
Figure 5:
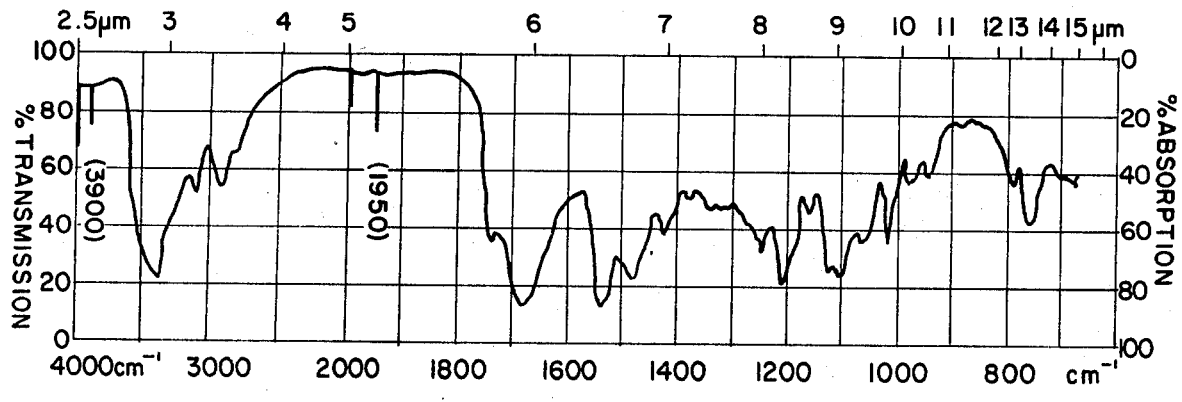
Figure 6:
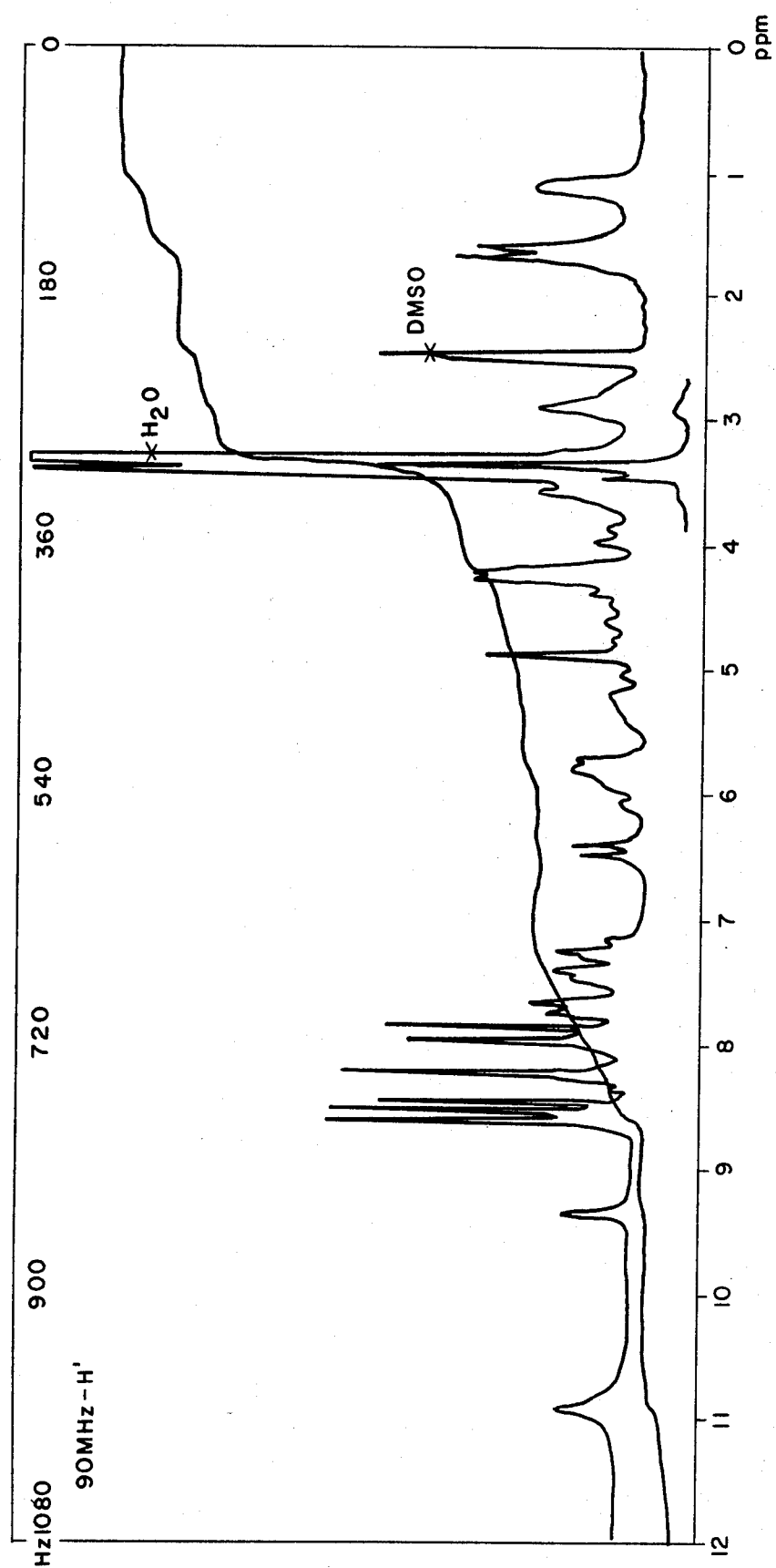

Light yellow amorphous powder
M.P.>310°
Analysis: Found (1) C 48.5, H 3.8, N 12.4%, (2) C 50.3, H 4.3, N 12.4, O 21.7, S 12.0%, i.e. carbon content ca 48.5–50.3%, hydrogen content 3.8–4.3%,
UV spectrum in acetonitrile, see FIG. 4.
λmax 218 nm log $\epsilon'=1.90$, 293 nm log $\epsilon'=1.40$, 362 nm log $\epsilon'=1.16$.
IR spectrum (in KBr), see FIG. 5.
$^1$H-NMR spectrum in DMSO, 90 MHz with tetramethylsilane as internal standard, see FIG. 6.

Solubility

Slightly soluble in dimethylformamide, acetonitrile, dioxane, pyridine, dimethylsulphoxide, fairly soluble in chloroform; sparingly soluble in methanol, ethanol and insoluble in water and hexane.

Amino acid analysis

Aside from non-identified amino acids, the amino acid analysis revealed an amino acid having the same retention time as threonine.

S 54832/A-III

Figure 7:
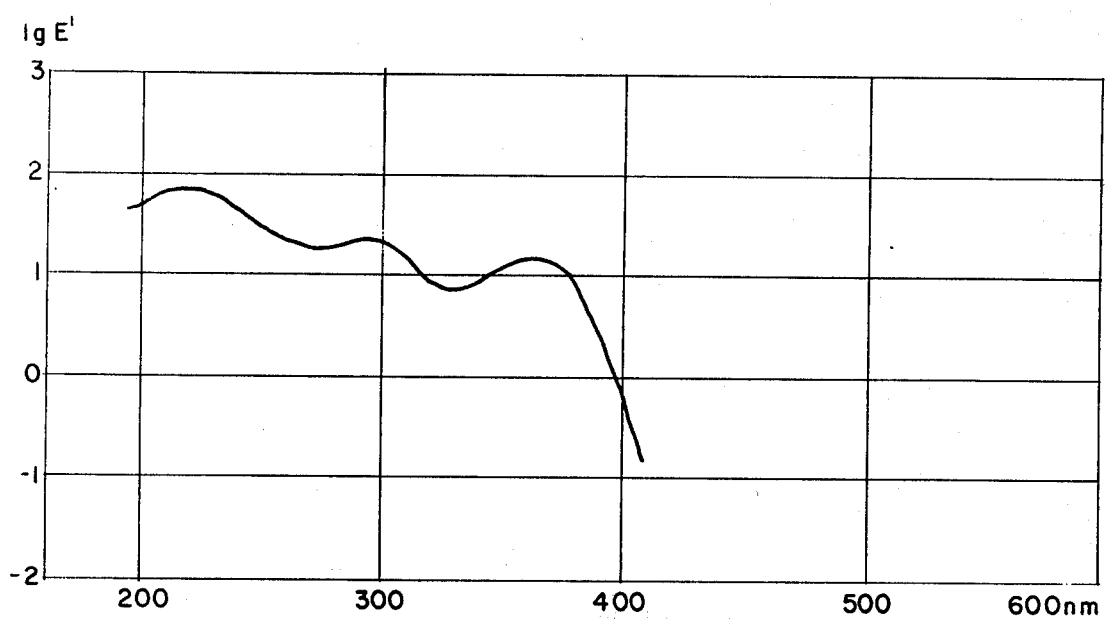
Figure 8:
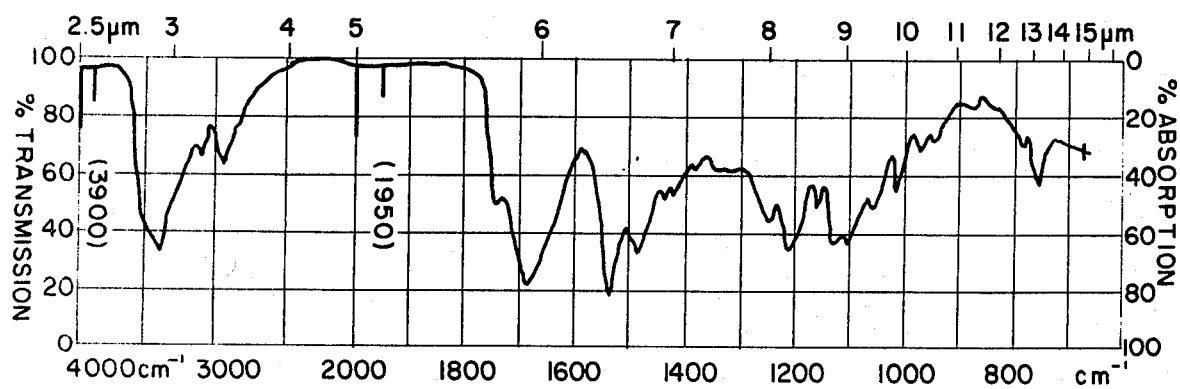
Figure 12:
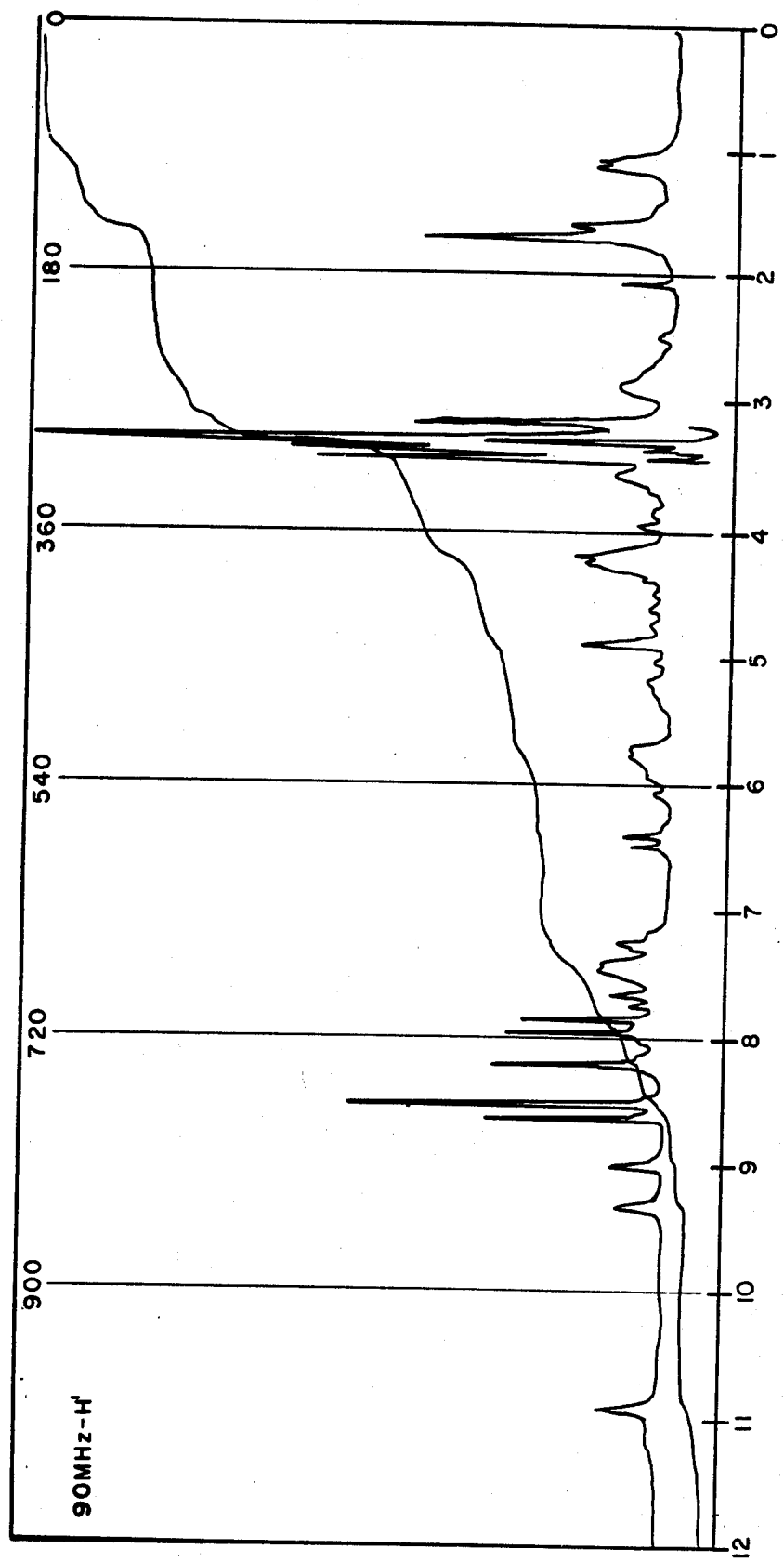

Light yellow amorphous powder
M.P.>310°
Analysis: Found (1) C 48.1, H 4.1, N 12.3%, (2) C 49.9, H 4.3, N 12.5, S 11.5, O 21.8%.
UV spectrum in acetonitrile, see FIG. 7.
λmax 218 nm log $\epsilon'=1.86$, 292 nm log $\epsilon'=1.36$, 362 nm log $\epsilon'=1.14$.
IR spectrum (in KBr), see FIG. 8. $^1$H-NMR (conditions as for S 54832/A-II) see FIG. 12.

Solubility

Slightly soluble in dimethylformamide, acetonitrile, dioxane, pyridine, dimethylsulphoxide; fairly soluble in chloroform; sparingly soluble in methanol, ethanol and insoluble in water and hexane.

Amino acid analysis

Aside from non-identified amino acids, the amino acid analysis revealed an amino acid having the same retention time as threonine.

S 54832/A-IV

Light yellow amorphous powder
M.P. > 310°
$[\alpha]_D^{20} = +153.2°$ (c = 0.752 in pyridine)
Formula $C_{59}, H_{57}, N_{13}, O_{19}, S_5$ (1412.52)
Analysis: Found C 49.0, H 4.0, N 12.7, O 21.8, S, 11.6% Calculated C 50.2, H 4.1, N 12.9, O 21.5, S 11.3.

Figure 9:
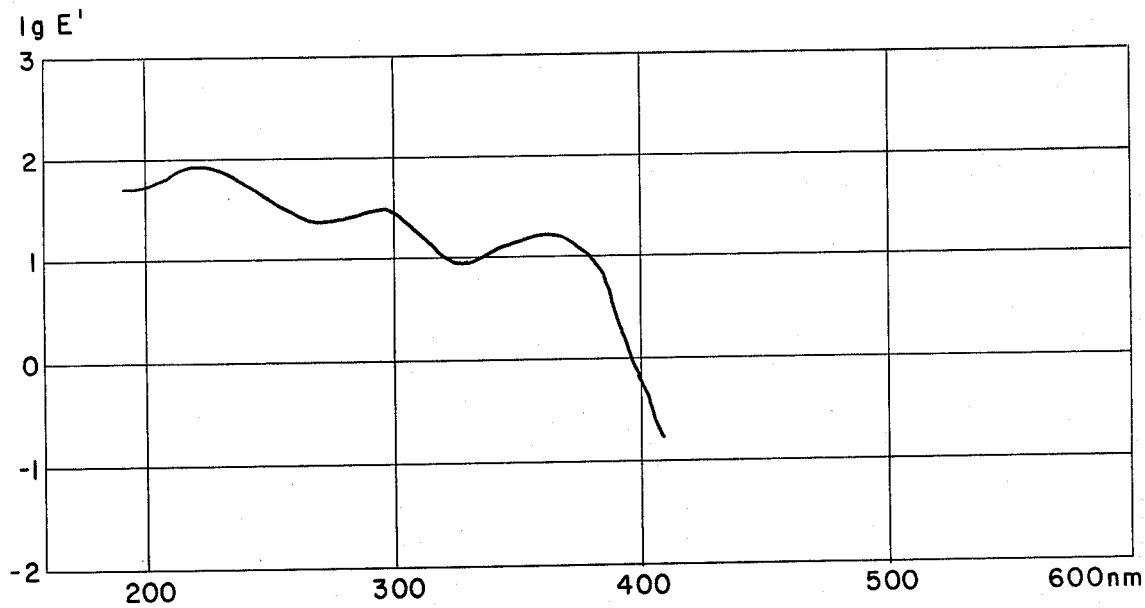

UV spectrum in acetonitrile, see FIG. 9. $\lambda$max 218 nm log $\epsilon' = 1.88$, 292 nm log $\epsilon' = 1.41$, 360 nm log $\epsilon' = 1.15$.

Figure 10:
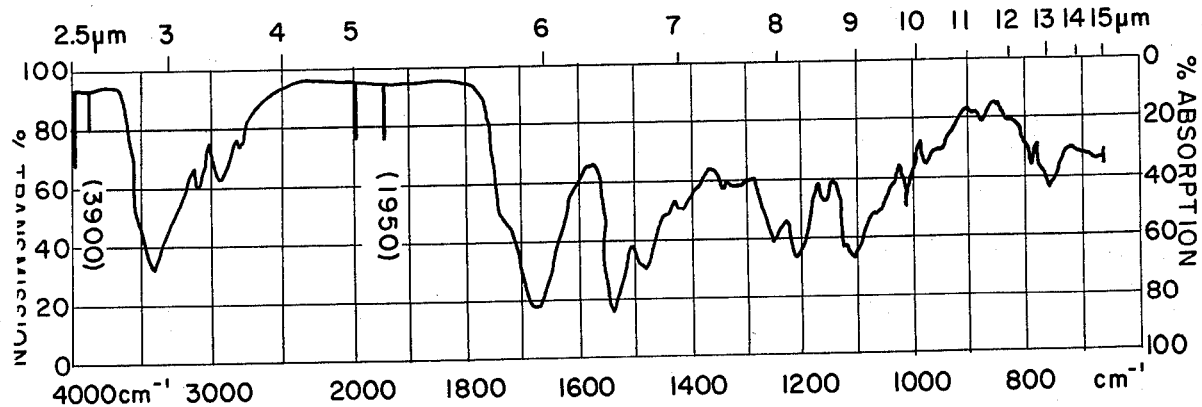

IR spectrum (in KBr), see FIG. 10.

Figure 11:
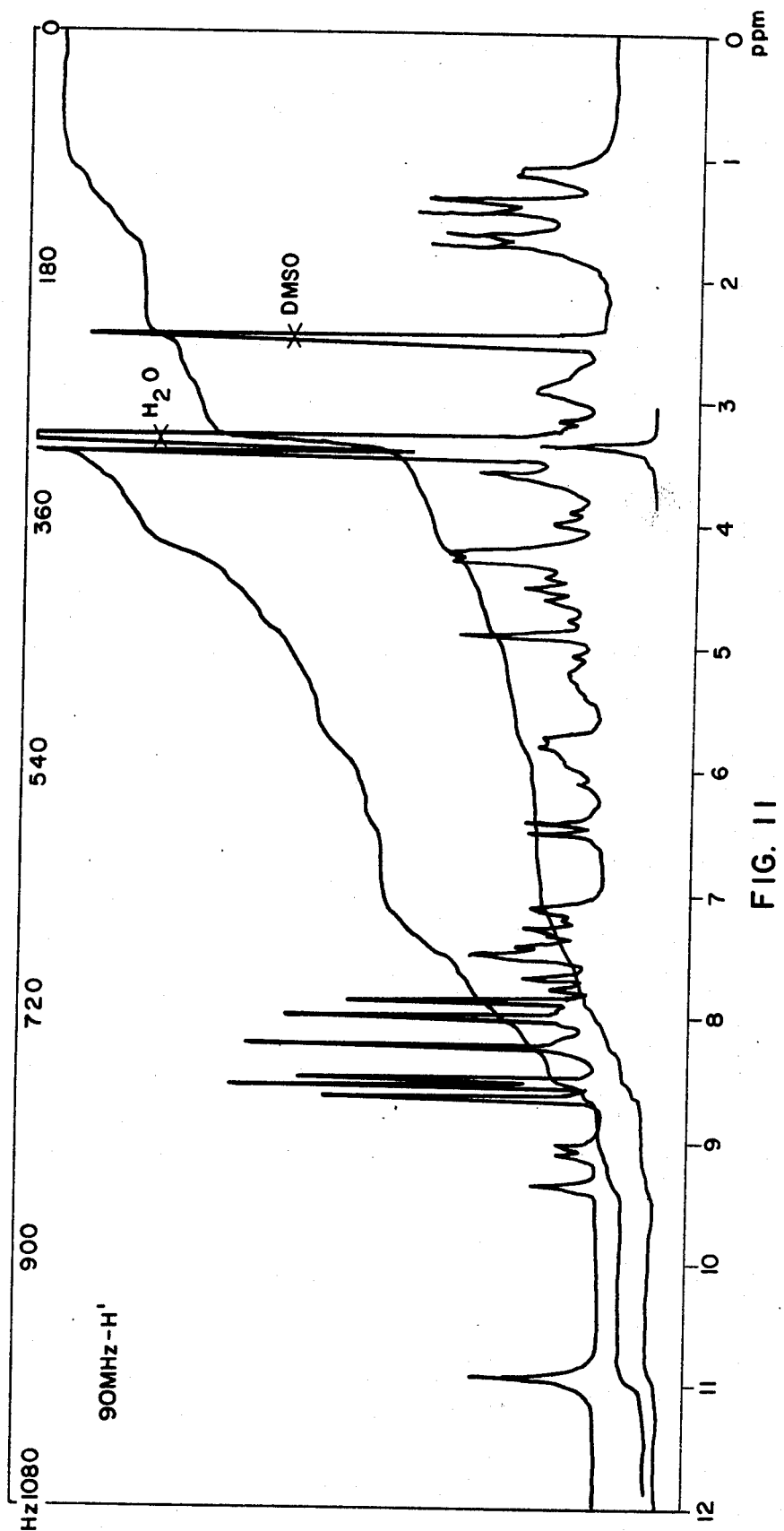

$^1$H-NMR spectrum in DMSO, 90 MHz with tetramethylsilane as internal standard, see FIG. 11.

$^{13}$C-NMR spectrum in DMSO on a BRUKER HX-90E spectrometer at 22.63 MHz (internal standard TMS = 0 ppm), see the following Table II.

Solubility

Slightly soluble in dimethylformamide, acetonitrile, dioxane, pyridine, dimethylsulphoxide; fairly soluble in chloroform, sparingly soluble in methanol, ethanol and insoluble in water and hexane.

Amino acid analysis

Aside from non-identified amino acids, the amino acid analysis revealed amino acids having the same retention time as threonine and alanine.

TABLE II $^{13}$C—NMR spectrum of S 54832/A-IV
100 mg in 1.2 ml DMSO + TMS

| |
|---|
| 174.95 |
| 172.22 |
| 169.36 |
| 168.84 |
| 168.38 |
| 168.06 |
| 164.81 |
| 161.95 |
| 161.17 |
| 160.46 |
| 154.87 |
| 151.68 |
| 151.36 |
| 150.45 |
| 149.54 |
| 148.50 |
| 143.82 |
| 136.02 |
| 135.69 |
| 131.02 |
| 130.30 |
| 129.20 |
| 128.61 |
| 127.51 |
| 126.40 |
| 125.30 |
| 124.13 |
| 121.07 |
| 120.42 |
| 113.34 |
| 112.17 |
| 96.57 |
| 80.65 |
| 75.90 |
| 74.60 |
| 70.51 |
| 68.43 |

TABLE II-continued $^{13}$C—NMR spectrum of S 54832/A-IV
100 mg in 1.2 ml DMSO + TMS

| |
|---|
| 66.28 |
| 65.80 |
| 64.80 |
| 64.14 |
| 61.93 |
| 58.55 |
| 57.06 |
| 50.88 |
| 49.39 |
| 46.53 |
| 26.84 |
| 19.10 |
| 14.55 | pK and equivalent weight determination $pK_1 = 7.31$; (approximate equivalent weight 1554) $pK_2 \geq 10.70$; obtained when 6.406 mg of S 54832/A-IV dissolved in 2 ml methylcellosolve/water (84:16) were titrated with 0.1N tetramethylammonium hydroxide.

In the following Table III $R_f$ values of S 54832/A-I, S 54832/A-II, S 54832/A-III and S 54832/A-IV on thin layer chromatography are indicated, with Nosiheptide (compound N) as a reference substance (silicagel Merck 60 plates, layer thickness 0.25 mm, running distance 14.7 cm).

TABLE III

| Solvent system | $R_f$ values | | | | |
| --- | --- | --- | --- | --- | --- |
| | A-I | A-II | A-III | A-IV | N |
| Methylene chloride/methanol/water (80:17.5:2) | 0.54 | 0.44 | 0.49 | 0.44 | 0.49 |
| Methylene chloride/methanol/water (88:11:1) | 0.40 | 0.28 | 0.32 | 0.27 | 0.32 |

(Nosiheptide has the same Rf values as S 54832/A-III, but differs in analysis data, and u.v. and i.r. spectra).

Iodine vapour may be used to detect the compounds. After the plate has been sprayed with 0.2% Ce(SO$_4$)$_2$ solution in 50% sulphuric acid and heated to 130°, S 54832/A-I to IV show up as a grey-brown colouration. The compounds all show up as a yellow fluorescent colouration under 366 nm light without any detection agent.

The process according to the invention may be effected by known methods. A preferred strain of *Micromonospora globosa* capable of producing S 54832/A-I, S 54832/A-II, S 54832/A-III and S 54832/A-IV forms part of the present invention and has been deposited with the United States Department of Agriculture (Northern Utilization Research and Development Division) Peoria, Ill. USA on Apr. 26, 1978 and is freely available as the culture NRRL 11299. The same culture was deposited with the American Type Culture Collection (ATCC) Rockville, Md., USA, on Dec. 8, 1978 and is freely available as the culture ATCC 31465. The culture is also available from Sandoz AG, Basel, Switzerland.

However, S 54832/A-I, S 54832/A-II, S 54832/A-III and/or S 54832/A-IV producing strains may be used which may be obtained from the above-mentioned strain of *Micromonospora globosa* by mutation by e.g. radiation, treatment with conventional mutagenic substances, or by selection.

Characteristics of the strain ATCC 31465 or NRRL 11299

This strain was isolated from a fresh soil sample from a rice field in Cullera, Spain, in 1976. From the key in Bergey's Manual 8th Edition p 846 et seq the strain ATCC 31465 or NRRL 11299 may be identified as being of the Micromonosporaceae family, of the Microspora genus and of the *Micromonospora globosa* species, but differs and is further characterised as follows: The culture does not form aerial mycelia and grows as a substrate or vegetative mycelial mass in discrete but elevated orange-coloured colonies of irregular shape. The mycelia having a diameter of between 0.5 µm and 0.7 µm are straight to slightly wavy and carry lateral and terminal spores. The lateral spores appear often singly, but there are also sometimes double spores arranged one above the other with the lower ones being larger. There are occasionally two spores at the end of a sporophore. The spores are elliptical to oval or round with a diameter of 1.0 to 1.3 µm. In most agar media the vegetative mycelia are moderately yellow-pink or light-apricot coloured and soft having a tendency towards fragmentation, however, not like the species *Nocardia*. In some media irregular swellings are observed, which are bulb-like structures which may reach two to three times the size of spores. It is thought that these are involuntary forms that appear in other Actinomycetes species. On a sucrose medium the spores appear as grape-like clusters while on all other media the spores appear in either single or double form and are carried by relatively long sporophores (2–3 µm). The strain grows only poorly on synthetic media, breaks down only three of the sugars studied and grows very well on media with complex protein-containing substances. The cultural properties of the strain on normal biological media and its carbon utilization are indicated in the following Tables:

| Culture medium | Cultural properties cultural characteristics | aerial mycelium form |
|---|---|---|
| malt-yeast extract-agar | g: excellent, orange<br>b: orange (R3ea)*<br>am: none<br>sp: none | — |
| oatmeal agar | g: moderate, orange<br>b: light-orange (R3ea)*<br>am: none<br>sp: none | — |
| starch- inorganic salts- agar | g: poor, light-orange<br>b: beige (R3ea)*<br>am: none<br>sp: none | — |
| glycerine-asparagine-agar | g: poor, light-orange<br>b: beige (R3ea)*<br>am: none<br>sp: none | — | g: growth
b: reverse side
am: aerial mycelia
sp: soluble pigments
*: reference to the "Colour-wheels system" (Tresner and Bachus, 1963)

| Growth | Utilization of carbon compounds<br>Carbon sources |
|---|---|
| + | D-cellobiose, cellulose, D-saccharose |
| — | D- and L-arabinose, dextrin, dulcitol, D-fructose, D-glucose, D-galactose, glycerine m-inositol, inulin, D-lactose, D-maltose, D-mannitol, D-mannose, D-melibiose, D-melezitose, D-raffinose, D-ribose, L-rhamnose, D-salicin, D-sorbitol, D-xylose, starch |

+: poor carbon utilization
—: no carbon utilization

The strain possesses the following physiological properties:

| | |
|---|---|
| nitrate reduction | negative |
| starch hydrolysis | positive (weak) |
| cellulose decomposition | positive (weak) |
| tyrosine reaction | negative (pink soluble pigment) |
| milk coagulation | positive |
| milk peptonisation | positive (slow) |
| gelatine liquefaction | negative |
| melanine formation | negative (grows on medium) |

The new strain may be grown on different culture media with conventional nutrients e.g. as described in the Examples below. The strain may be cultivated as an aerobic surface culture or an immersion culture.

As soon as the maximum amount of S 54832/A-I, S 54832/A-II, S 54832/A-III and/or S 54832/A-IV has been produced in the culture, which may e.g. be ascertained by the activity towards *Staphylococcus aureus*, the mycelium may be separated from the culture broth and extracted. The compounds present in the culture filtrate may be obtained by extraction with a water-immiscible organic solvent, e.g. ethyl acetate, butyl acetate, and n-butanol. Alternatively the mycelium portion in the culture broth may be homogenized, e.g. with an Ultraturrax. The compounds may be extracted using any of the above-mentioned solvents.

A preferred isolation procedure comprises separating the broth by centrifuging and/or filtering into mycelium and culture filtrate. The mycelium may then be extracted by means of a Turrax apparatus with methanol or acetone. The cell material may be centrifuged off and the methanol or acetone evaporated whilst water is added to give an aqueous mixture.

Subsequently extraction is effected with a water-immiscible organic solvent, e.g. n-butanol or ethyl acetate, and the extracts are concentrated by evaporation at a low temperature, preferably at 40°–50°, in a vacuum. The amount of active compounds remaining in the culture filtrate may be extracted with the above-mentioned solvents. The compounds S 54832/A-I, S 54832/A-II, S 54832/A-III and/or S 54832/A-IV may be isolated and purified from the resulting crude extracts by chromatographic methods known per se. Precipitation of the crude extracts with petroleum ether as a first step proved to be advantageous, as lipophilic impurities can be removed.

The pure compounds S 54832/A-I to A-IV may be obtained from the precipitation product initially by gel filtration on Sephadex $LH_{20}$ and subsequent repeated chromatography on silicagel. The compounds precipitate as light-yellow amorphous powders; after 15 hours drying in a high vacuum at 20° each compound has a M.P. of >310° (decomp).

The invention also provides fermentation broths obtained during the growth of an S 54832/A-I and/or S 54832/A-II and/or S 54832/A-III and/or S 54832/A-IV producing strain e.g. of *Micromonospora globosa*.

The compounds S 54832/A-I, S 54832/A-II, S 54832/A-III and S 54832/A-IV exhibit antibiotic activity. They exhibit a growth inhibiting effect towards microorganisms such as gram-positive bacteria, mycoplasms and neisseriae, but no activity towards yeast and fungi.

The very wide activity towards gram-positive bacteria includes pathogenic representatives such as Staphylococci, Streptococci, Corynebacteria and Mycobacteria. The following Table indicates the minimum inhibition concentration (MIC) of S 54832/A-I to IV against various microorganisms. The MIC values are determined in known manner in the series dilution test, effected by incubation in Trypticase Soya Broth at 37° for 24 hours. Inoculum density: $10^5$ germs/ml.

| Organism | MIC/μg/ml - S 54832 | | | |
|---|---|---|---|---|
| | /A-I | /A-II | /A-III | /A-IV |
| Staphylococcus aureus | 0.03 | ≦0.01 | 0.019 | ≦0.01 |
| Staphylococcus aureus res. Penicillin | 0.03 | | | 0.03 |
| Staphylococcus aureus res. Tetracycline | ≦0.01 | ≦0.01 | 0.019 | 0.03 |
| Staphylococcus aureus res. Rifamycin | 0,03 | | | 0.03 |
| Staphylococcus aureus 6538P | 0.03 | | | 0.03 |
| Staphylococcus aureus | ≦0.01 | | | ≦0.01 |
| Streptococcus aronson | 0.03 | 0.08 | 0.038 | 0.03 |
| Streptococcus faecalis | 0.1 | 0.15 | 0.15 | 0.1 |
| Streptococcus faecalis | 0.03 | 0.038 | 0.15 | 0.1 |
| Streptococcus pyogenes | 0.1 | | | 1 |
| Streptococcus faecalis | 0.03 | | | 0.3 |
| Streptococcus haemolyticus | 0.1 | | | 1 |
| Diplococcus pneumoniae | 0.1 | | | 1 |
| Corynebacterium equi | 0.03 | | | 1 |
| Sarcina lutea res. Erythromycin | ≦0.01 | | | ≦0.01 |
| Bacillus subtilis | ≦0.01 | | | 1 |
| Clostridium sphenoides | 0,3 | | | 0,3 |
| Clostridium pasteurianum | ≦0.01 | | | 0,03 |
| Mycobacterium thamnophesos | ≦0.01 | | | 0.1 |
| Mycobacterium smegmatis | ≦0.01 | | | 0.1 |
| Mycoplasma laidlawii | 0.03 | | | 0.03 |
| Neisseria catharalis | 0.1 | | | 0.3 |
| Neisseria pharyngis | ≦0.01 | ≦0.01 | 0.15 | 0.03 |

The growth inhibiting effect against *Streptococcus pyogenes* and *pneumoniae*, and *Staphylococcus aureus* is also observed in vivo in the mouse on parenteral administration of from about 0.2 to about 50 mg/kg.

The compounds S 54832/A-I, S 54832/A-II, S 54832/A-III and S 54832/A-IV are therefore useful as antibiotics.

For the above mentioned use the dosage will, of course, vary depending on the compound employed, mode of administration and condition to be treated. However, in general, satisfacory results are obtained when administered at a daily dosage of from 0.1 mg to about 50 mg per kg animal body weight, conveniently given in divided doses 2 to 4 times a day or in sustained release form. For the larger mammal, the total daily dosage is in the range from about 10 to about 3500 mg, e.g. up to 500 mg. Dosage forms suitable for oral administration comprise from about 2 mg to about 250 mg of the compounds admixed with a solid or liquid pharmaceutical carrier or diluent. Dosage forms suitable for parenteral administration comprise from about 2 to about 20 mg of the compounds admixed with a liquid pharmaceutical carrier or diluent.

The compounds may be administered alone, in the form of a pharmaceutical composition for enteral, parenteral or topical administration or mixed with animal feed. The present invention therefore provides a pharmaceutical composition comprising S 54832/A-I, S 54832/A-II, S 54832/A-III or S 54832/A-IV in association with a pharmaceutical carrier or diluent. Such compositions may be formulated in conventional manner to be, for example, a solution or a tablet. The present invention also comprises an animal feed incorporating S 54832/A-I, S 54832/A-II, S 54832/A-III or S 54832/A-IV preferably in a concentration of from 1 to 500 mg per kg of feed.

In the following Examples all temperatures are indicated in degrees Centigrade. All parts used herein are by volume except where otherwise stated. N-Z Amine Type A is a pancreatic hydrolysate of casein obtained from Sheffield Chemical, Union, N.J., USA.

EXAMPLE 1

Fermentation in an shaken culture (a) Agar starting culture

The agar culture of the strain ATCC 31465 or NRRL 11299 used as starting material is obtained by inoculating a culture medium (I) of the following compositions:

| | g/liter |
|---|---|
| glucose | 10.0 |
| soluble starch | 20.0 |
| N—Z—amine Type A | 5.0 |
| CaCO$_3$ | 1.0 |
| yeast extract | 5.0 |
| agar (Bacto) | 15.0 |
| distilled water | to 1 liter | with a spore suspension of the originally isolated strain ATCC 31465 or NRRL 11299 produced in manner known per se. The medium is adjusted to pH 7.0 with NaOH before the sterilisation and has a pH of 6.8 to 7.0 after the sterilisation (20 minutes at 120° C.).

(b) Spore suspension 5 ml of a sterile 0.9% (w/v) common salt solution is added to a well sporulating agar starting culture of the strain ATCC 31465 or NRRL 11299. A dense spore suspension results.

(c) Pre-culture and intermediate culture 5 ml of this spore suspension are used for inoculation of 50 ml of the following pre-culture medium (II) in a 200 ml Erlenmeyer flask:

| | g/liter |
|---|---|
| dextrin | 10.0 |
| glucose | 10.0 |
| peptone | 5.0 |
| yeast extract | 5.0 |
| CaCO$_3$ | 1.0 |
| distilled water | to 1 liter |

The pH value is adjusted to 7.2 with NaOH. The preculture medium is sterilised in an autoclave at 120° for 20 minutes, which results in a final pH value of 7.0 to 7.2.

The thus obtained pre-culture is incubated aerobically for 4 days at 27° on a rotary mechanical shaker (100 r.p.m.) and is used for the inoculation of a second pre-culture by inoculating 100 ml of the following medium (III):

|  | g/liter |
| --- | --- |
| meat extract | 3.0 |
| tryptone | 5.0 |
| glucose | 1.0 |
| soluble starch | 24.0 |
| yeast extract | 5.0 |
| CaCO₃ | 2.0 |
| distilled water | to 1 liter | by 5 ml of the pre-culture in a 500 ml Erlenmeyer flask.

The pH value is adjusted with NaOH to 7.2 and the medium is sterilised in an autoclave at 120° for 20 minutes, whereupon the final pH value is 7.0 to 7.2.

(d) Main culture

The intermediate culture is aerobically incubated for 3 days at 27° on a rotary mechanical shaker (220 r.p.m.) and is then used directly for the inoculation of main culture by inoculating with 100 ml of the following medium (IV):

|  | g/liter |
| --- | --- |
| soluble starch | 20.0 |
| yeast extract | 10.0 |
| glucose | 10.0 |
| casein hydrolysate | 5.0 |
| calcium chloride di-hydrate | 4.0 |
| cobalt (II) chloride | 0.00013 |
| distilled water | to 1 liter | by 5 ml of the intermediate culture in a 500 ml Erlenmeyer flask.

The pH value is adjusted to 7.2 with NaOH and the medium is sterilised in an autoclave at 120° for 20 minutes, whereupon the final pH value is 6.8 to 7.0. The thus obtained main culture is incubated for 5 days at 27° on a rotary mechanical shaker (220 r.p.m.).

EXAMPLE 2

Cultivation in a fermenter

The spore and mycelium suspension used for inoculation of the pre-culture is produced from a culture of the originally isolated strain ATCC 31465 or NRRL 11299, which was obtained after 21 days at 27° on an agar medium of the following composition:

|  | g/liter |
| --- | --- |
| soluble starch | 20 |
| glucose | 10 |
| yeast extract | 5 |
| N—Z—amine Type A | 5 |
| CaCO₃ | 1 |
| agar | 15 |
| distilled water | to 1 liter |

The spores and mycelium of this culture are taken up in physiological saline.

50 ml of this suspension are used for the inoculation of each of five 2 liter Erlenmeyer flasks each containing 1 liter of medium of the following composition:

|  | g/liter |
| --- | --- |
| dextrin | 10 |
| glucose | 10 |
| peptone | 5 |
| yeast extract | 5 |
| CaCO₃ | 1 |
| distilled water | to 1 liter | and are incubated on a rotary mechanical shaker (180 r.p.m.) r=5 cm) for 4 days at 27°. The pH value of the nutrient solution is adjusted to 7.2 with NaOH before sterilisation. 5 liters of this pre-culture are used for the inoculation of a 50 liter medium of the following composition:

|  | g/liter |
| --- | --- |
| soluble starch | 24 |
| tryptone | 5 |
| yeast extract | 5 |
| meat extract | 3 |
| CaCO₃ | 2 |
| glucose | 1 |
| distilled water | to 1 liter | in a 75 liter steel fermenter. This intermediate culture is incubated for 3 days at 27° with stirring (200 r.p.m., paddle-stirrer), under aeration (1 liter air/liter medium/minute) and at a elevated pressure of 0.5 bar.

The main culture is fermented with stirring (110 r.p.m., paddle-stirrer) and aeration (1 liter air/liter medium/minute) for 4 days at 27° and 0.5 bar elevated pressure in a 750 liter fermenter containing 500 liters of nutrient solution of the following composition:

|  | g/liter |
| --- | --- |
| soluble starch | 20 |
| yeast extract | 10 |
| glucose | 10 |
| casein hydrolysate | 5 |
| calcium chloride di-hydrate | 4 |
| cobalt (II)-chloride | 0.00013 |
| demineralised water | to 1 liter |

The pH value is also adjusted at this stage of the process with NaOH to 7.2 before sterilisation.

EXAMPLE 3

Isolation of the compounds S 54832/A-I, S 54832/A-II, S 54832/A-III and S 54832/A-IV 470 liters of fermentation broth (obtained according to Example 2) are adjusted to pH 7.0 with 2N NaOH and are separated with a Westfalia separator giving 450 liters of culture filtrate and 22 kg of mycelium precipitate. The culture filtrate is extracted three times each with 500 liters of ethyl acetate. After the combined organic extracts are washed with 50 liters of water the organic phase is concentrated by evaporation of dryness at a temperature of 20°–50°. 117 g of oily crude product are obtained.

The mycelium is homogenized once with 70 liters of methanol for one hour and then once with 70 liters of 90% methanol for one hour, using an Ultra-Turrax apparatus. The methanolic extracts obtained after filtration with suction of the solid substances are combined and are concentrated by evaporating off the methanol whilst adding water giving approximately 150 liters of an aqueous mixture which is extracted three times each with 200 liters of ethyl acetate and the combined extracts are washed with 100 liters of water. The combined extracts are concentrated by evaporation to dryness as above and yield 66 g of crude oily extract.

The 183 g of combined oily extracts are added to 1 liter of petroleum ether with stirring. The supernatant solution is decanted off and the solvent is removed in a vacuum at 50° to give an oily residue. The precipitation product is then dissolved in methylene chloride/methanol (1:1) and the solution is applied to a column of 1.5 kg of Sephadex LH$_{20}$ prepared with methylene chloride/methanol (1:1). Elution with methylene chloride/methanol (1:1) yields 11.5 g of material after removal of solvent, having an activity towards Staphylococcus aureus. This material is dissolved in methylene chloride/methanol/water (88:11:1) and the solution is applied to a column of 1 kg of silicagel Merck (grain size 0.063–0.2 mm) prepared with methylene chloride/methanol/water (88:11:1). Elution with methylene chloride/methanol/water (88:11:1) yields initially 984 mg of considerably enriched S 54832/A-I solids. The later fractions yield, after evaporating the solvent in a vacuum, a mixture of S 54832/A-II, S 54832/A-III, S 54832/A-IV and inactive impurities. The S 54832/A-I solids (984 mg) are dissolved in 50 ml of methylene chloride/methanol (1:1) and concentrated by evaporation to approximately 20 ml, whereupon S 54832/A-I precipitates. The substance is filtered off and is washed with methanol. S 54832/A-I is obtained as amorphous, light yellow powder. M.P.>310° (after 15 hours drying in a high vacuum at room temperature).

In order to isolate S 54832/A-II, S 54832/A-III and S 54832/A-IV in pure form the above mixture of the three compounds (594 mg) is dissolved in methylene chloride/methanol water (92:7.5:0.5) and the solution is applied to a column of 500 g of silicagel Merck (grain size 0.04–0.063 mm) prepared with methylene chloride/methanol/water (92:7.5:0.5), whereupon initially S 54832/A-II, then S 54832/A-III and then S 54832/A-IV are eluted.

The final purification of the compounds is effected by precipitation from methanol in analogous manner as described for S 54832/A-I.

The pure substances of S 54832/A-II, S 54832/A-III and S 54832/A-IV precipitate as amorphous light yellow powders and have all a M.P.>310° (after 15 hours drying in a high vacuum at room temperature).

EXAMPLE 4

In analogous manner to Example 3, the compounds S 54832/A-I to IV may be produced from the fermentation broth of Example 1.

The structure of S 54832/A-I is as follows:

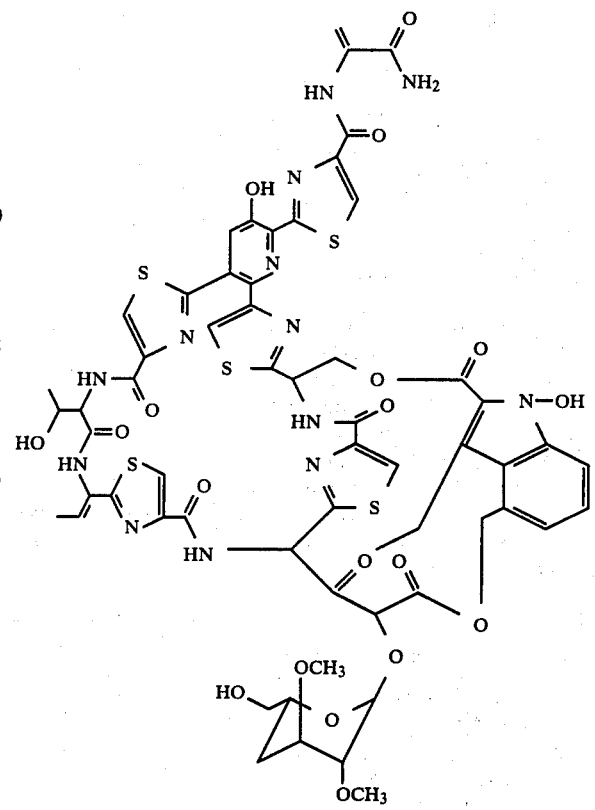

The structure of S 54832/A-IV is as follows:

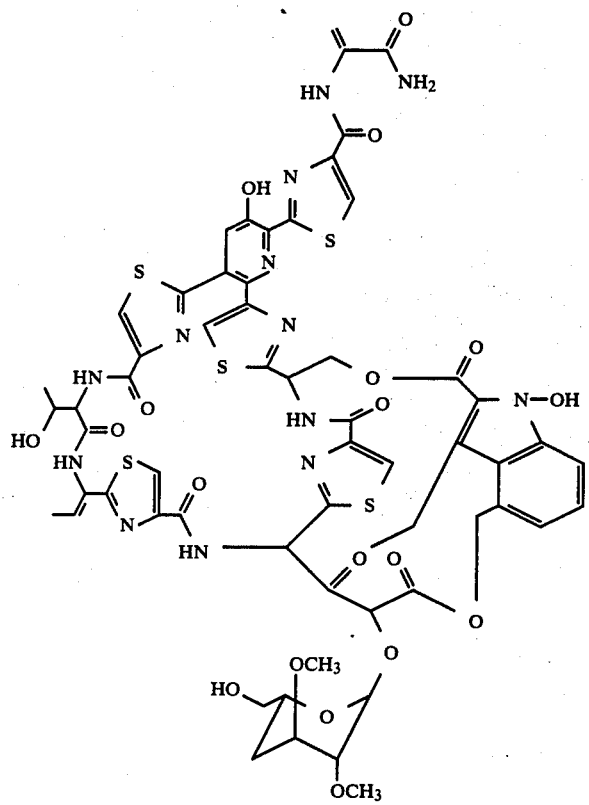

What we claim is:

1. A compound selected from the group consisting of S 54832/A-I having the structure

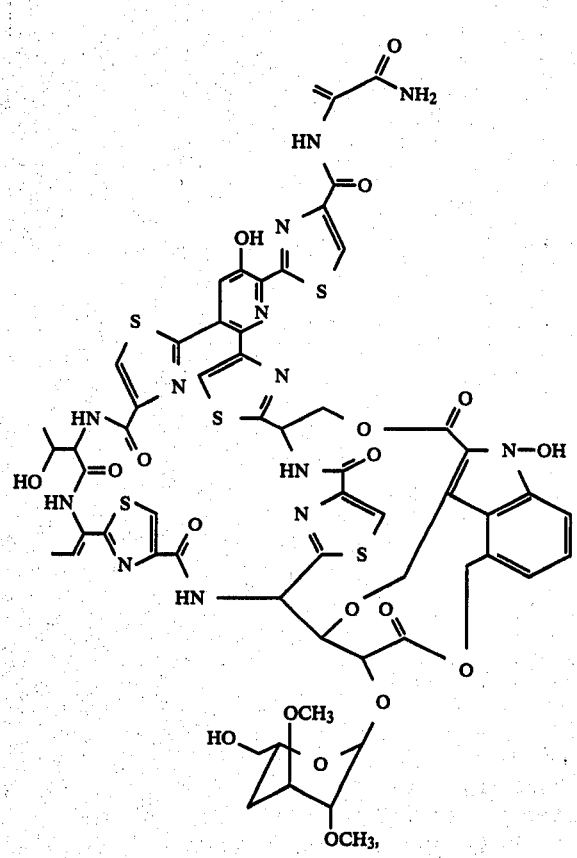

S 54832/A-II having the following characterising features:
(i) light yellow when in solid form,
(ii) Analysis (i) C 48.5, H 3.8, N 12.4%, (ii) C 50.3, H 4.3, N 12.4, O 21.7, S 12.0%,
(iii) UV spectrum in acetonitrile see FIG. 4,
(iv) IR spectrum (in KBr) see FIG. 5.
(v) Proton NMR spectrum in DMSO (90 MHz) see FIG. 6, and
(vi) antibiotic activity, S-54832/A-III having the following characterising features:
(i) light yellow when in solid form,
(ii) Analysis (1) C 48.1, H 4.1, N 12.3%, (2) C 49.9, H 4.3, N 12.5, S 11.5, O 21.8%,
(iii) UV spectrum in acetonitrile see FIG. 7,
(iv) IR spectrum (in KBr) see FIG. 8, and
(v) antibiotic activity, and S 54832/A-IV having the structure 2. S 54832/A-I having the structure

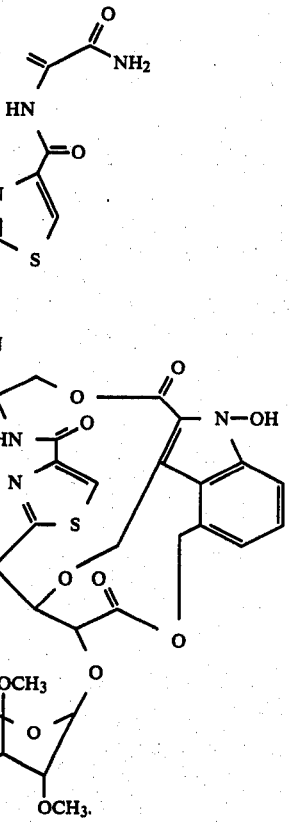

3. S 54832/A-IV having the structure

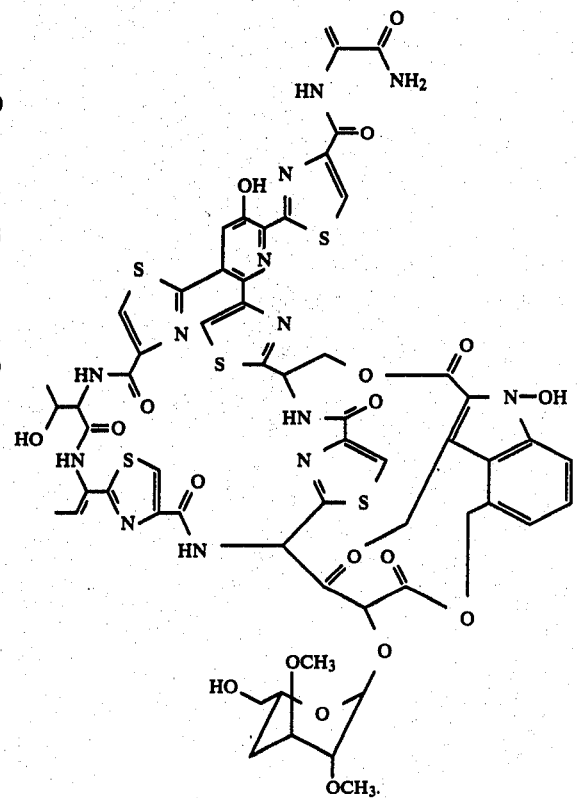

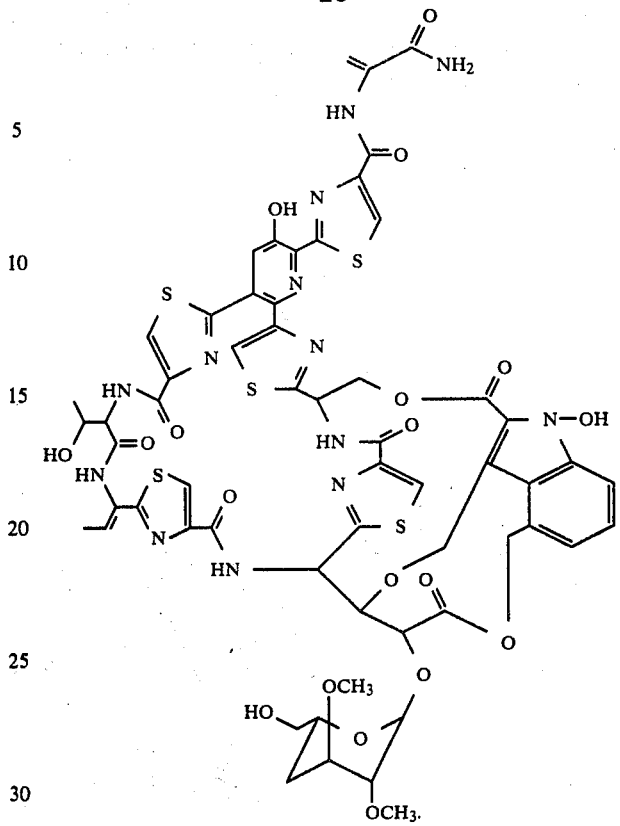

4. A pharmaceutical composition useful in combatting bacteria which comprises an antibacteria effective amount of a compound of claim 1 in association with a pharmaceutical carrier or diluent.

5. A method of combatting bacteria in hosts which comprises administering a therapeutically effective amount of a compound of claim 1 to a host in need of such treatment.

6. A fermentation broth prepared by cultivating a S 54832/A-I, S 54832/A-II, S 54832/A-III or S 54832/A-IV producing strain or mixtures thereof under aerobic conditions in a nutrient medium consisting essentially of S 54832/A-I, S 54832/A-II, S 54832/A-III or S 54832/A-IV or a S 54832/A-I, S 54832/A-II, S 54832/A-III or S 54832/A-IV producing strain or mixtures thereof and the nutrient medium.

* * * * *